United States Patent [19]
Unrug

[11] Patent Number: 5,476,492
[45] Date of Patent: Dec. 19, 1995

[54] BODY WARMER FOR THERAPEUTIC PURPOSES CONTAINING WHOLE HERB SEED

[76] Inventor: Sophia Unrug, 760 Fawcett Dr., Beavercreek, Ohio 45434

[21] Appl. No.: 199,855

[22] Filed: Feb. 23, 1994

[51] Int. Cl.$^6$ .................................................. A61F 7/00
[52] U.S. Cl. .................................................. 607/114
[58] Field of Search ........................ 607/96, 108–112, 607/114

[56] References Cited

U.S. PATENT DOCUMENTS

| | | | |
|---|---|---|---|
| 3,621,191 | 11/1971 | Cornwell | 607/111 |
| 3,632,966 | 1/1972 | Arron | 219/211 |
| 3,680,563 | 8/1972 | Forrest | 607/108 |
| 3,763,622 | 10/1973 | Stanley | 607/114 |
| 3,774,589 | 11/1973 | Kober | 607/114 |
| 3,780,537 | 12/1973 | Spencer | 607/114 |
| 3,889,101 | 6/1975 | Woods | 607/96 |
| 3,900,035 | 8/1975 | Welch et al. | 607/108 |
| 3,980,070 | 9/1976 | Krupa | 607/114 |
| 4,061,897 | 12/1977 | Thykeson | 607/108 |
| 4,207,885 | 6/1980 | Hampton et al. | 128/156 |
| 4,214,588 | 7/1980 | Byler | 607/111 |
| 4,324,785 | 4/1982 | Stevens | 424/195 |
| 4,335,725 | 6/1982 | Geldmacher | 128/399 |
| 4,335,726 | 6/1982 | Kolstedt | 128/400 |
| 4,462,224 | 7/1984 | Dunshee et al. | 607/114 |
| 4,488,552 | 12/1984 | McCann et al. | 607/112 |
| 4,505,271 | 3/1985 | Weber | 607/112 |
| 4,516,564 | 5/1985 | Koiso et al. | 607/114 |
| 4,573,447 | 3/1986 | Thrash et al. | 607/114 |
| 4,575,097 | 3/1986 | Brannigan et al. | 607/108 |
| 4,580,547 | 4/1986 | Kapralis et al. | 604/291 |
| 4,596,250 | 6/1986 | Beisang III et al. | 128/402 |
| 4,628,930 | 12/1986 | Williams | 607/108 |
| 4,657,531 | 4/1987 | Choi | 607/96 |
| 4,671,267 | 6/1987 | Stout | 607/114 |
| 4,700,706 | 10/1987 | Munch | 128/403 |
| 4,736,088 | 4/1988 | Bart | 607/112 |
| 4,747,841 | 5/1988 | Kuratomi et al. | 607/114 X |
| 4,753,241 | 6/1988 | Brannigan et al. | 607/112 |
| 4,756,311 | 7/1988 | Francis | 607/114 |
| 4,832,031 | 5/1989 | Last | 607/114 |
| 4,856,651 | 8/1989 | Francis | 607/114 |
| 4,887,368 | 12/1989 | Latzke | 607/114 |
| 4,904,846 | 2/1990 | Oscandal | 219/341 |
| 4,913,957 | 4/1990 | Strack et al. | 428/286 |
| 5,050,595 | 9/1991 | Kraft | 607/108 |
| 5,050,596 | 9/1991 | Walasek et al. | 607/111 |
| 5,050,598 | 9/1991 | Tucker | 607/111 |
| 5,058,563 | 10/1991 | Manker | 607/114 |
| 5,111,810 | 5/1992 | Fortney | 128/402 |
| 5,135,518 | 8/1992 | Vera | 604/291 |
| 5,174,285 | 12/1992 | Fontenot | 607/104 |
| 5,179,944 | 1/1993 | Mc Symytz | 607/114 |
| 5,205,278 | 4/1993 | Wang | 607/114 |
| 5,209,227 | 5/1993 | Deutsch | 607/104 |
| 5,230,333 | 7/1993 | Yates et al. | 607/114 |
| 5,233,987 | 8/1993 | Miyashita | 607/114 |
| 5,235,974 | 8/1993 | Miller | 607/108 |

FOREIGN PATENT DOCUMENTS

| 2029248 | 1/1990 | Japan | 607/114 |

*Primary Examiner*—Angela D. Sykes

[57] ABSTRACT

A method of enhancement of body heat production by application of whole seed of rubefacient mustard herbs of the Brassica genus and of herbs classified in the botanical family Cruciferae, in an anelastic breathable and pliable shell, whereby a balance between enhanced body heat production induced by whole seed of rubefacient herbs and heat dissipation is established, providing a steady warming effect without excessive heat build-up. A body warmer using the above method, comprising a shell of anelastic breathable and pliable material, divided into chambers containing whole seed of rubefacient herbs, and means of attachment to keep the warmer in place in desired area of human body.

2 Claims, 5 Drawing Sheets

BODY WARMER FOR THERAPEUTIC PURPOSES CONTAINING WHOLE HERB SEED

BACKGROUND

1. Field of Invention

This invention relates to body warmers, specifically to such warmers which are applied externally for joint and muscular pain relief and muscle relaxation.

2. Description of Prior Art

Drugstores commonly supply consumers with body warmers operating on a variety or principles. Originally the choice of body warmers was limited to water bottles and herbal preparations. The latter included infusions, decoctions, fomentations, poultices, salves, extracts and plasters. These preparations contained either active substances extracted from medicinal plants and herbs by hot water or alcohol, or herbal material ground to fine powder in order to enhance and accelerate the desired action of medicinal herbs. Warming plasters widely used in the past consisted of a piece of cloth coated on one surface with a glue mixed with powdered plant material such as red pepper (botanical name Capsicum) pods, or mustard (botanical name Brassica) seed. The warming plasters worked by rubefacient, action of powdered plant material causing reddening of skin and enhanced body heat production when applied directly to skin surface. These plasters could be applied for a limited time only to avoid excessive skin irritation and were unpleasant in use and especially during removal, as body hairs glued to the plaster were pulled out. The heating plasters have been abandoned altogether, and are no longer available on the market.

Thereafter inventors created several types of body heaters, including electric heaters, moist heating pads, microwaveable gel or fluid heaters, chemical heaters, and warmers retaining body heat.

In electric heaters, heat is produced by electric current flowing through a conductor of appropriate resistivity. The conductor is insulated and embedded in a flexible sheath that is:

(a) wrapped around the desired body part and fastened in place, for example U.S. Pat. No. 4,736,088 to Gordon B. Bart (1988)

(b) shaped as a piece of garment to warm a specific body part, for example U.S. Pat. No. 5,050,595 to Pam Krafft (1991) for women's breast warmers, and U.S. Pat. No. 4,628,930 to Steven N. Williams (1986) for a lower body warmer to prevent menstrual cramps.

(c) shaped as a cushion for use in the seated position; U.S. Pat. No. 4,335,725 to Barbara J. Geldmacher (1982).

(d) containing pouches or packs of heat retaining gel (for example U.S. Pat. No. 5,050,595 cited above) or oil, for example U.S. Pat. No. 4,904,846 to Augustin Oscandal (1990).

Most electric heaters are plugged to house electric current outlets. Some heaters, for example U.S. Pat. No. 5,050,595 cited above, use a portable battery as source of electricity for electric resistivity heating of gel packs that gradually release heat to the body.

Moist heating pads consist of a water absorbent fabric pad and wrap and fasteners to keep the wrap in place. The pad is heated in warm water, or moistened and heated in a microwave oven. The hot pad is then placed against the desired part of the body, wrapped around and fastened in place. The warming effect lasts until the heat stored in the moist pad is dissipated. U.S. Pat. No. 4,207,885 to Richard Hampton and P. Frank Hanes (1980), U.S. Pat. No. 4,753,241 to Patrick J. Brannigan and Gerald L. Peckich (1988), and U.S. Pat. No. 5,135,518 to Barbara Vera (1992) are examples of this type of warmers.

Microwaveable gel, and fluid heaters contain a pouch filled with gel, or fluid of high specific heat capacity, that is heated in a microwave oven and applied to the body. The pouch gradually releases heat for a period of time typically lasting about one hour. The gel pouch is shaped as a pad fastened to the desired part of the body by wrapping a bandage—for example U.S. Pat. No. 4,935,550 to Wayne K. Dunshee (1988), U.S. Pat. No. 4,756,311 to Sam E. Francis Jr. (1988), and U.S. Pat. No. 4,700,706 to Walter Munch (1987).

Other inventors proposed specially shaped pouches containing the heating gel or fluid to fit specific parts of the body. Heaters for feet, for example U.S. Pat. No. 5,050,598 to Dalton J. Tucker (1991), use a bladder fitting inside a slipper or other footwear, or flexible elastic tubing, U.S. Pat. No. 4,214,588 to William H. Byler (1980). Hand mitts for hot or cold therapy—U.S. Pat. No. 5,050,596 to Steven P. Walasek and Stuart J. Walasek (1991) use pockets filled with gel and insulating pockets with dead air space.

Chemical heaters are made in various shapes. They comprise pad or pouches filled with chemical compounds that produce heat. U.S. Pat. Nos. 5,176,134 to Gary C. Hudson (1993); 4,580,547 to Imants P. Kapralis and Harry Krukle (1986); 4,596,250 to Arthur A. Beisang, III, Robert A. Ersek, and Arthur A. Beisang (1986), and 5,046,479 to Akio Usui (1991) are examples of this type of heaters.

The warmers retaining body heat are made of a variety of fabrics consisting of a mix of natural and man-made fibers. Some use a mix of olefin, acrylic, wool and rubber elastane fibers. Other are made of a heat-reflecting metalized fabric facing the body and an artificial fiber fleece back. These warmers come in various shapes as gloves, sleeves and pads. They operate on the principle of retaining body heat and contain no source of heat external to the body. Some comprise a skin contact layer of absorbent fabric impregnated with treatment liquid, for instance U.S. Pat. No. 4,913,957 to David C. Strack and La Donna H. Brown (1990).

All these body warmers suffer from a number of disadvantages:

a) The electric body warmers using house current require wiring that must be plugged to a wall outlet. This reduces the mobility of the user of the warmer. Electric body warmers are unsuitable for overnight use, because wiring may be inadvertently entangled and broken during sleep. If placed under the body, the electric warmer may cause excessive heat, burning and blistering. Warnings to that effect are printed on packaging of electric body warmers currently on the market. Electric warmers combining a battery as a source of electricity and an electrically heated gel pouch do not reduce the mobility of the user but being bulky and heavy are inconvenient to use.

(b) The action of moist heating pads is of limited duration. They are inconvenient to use, as they require handling of pads while hot. The heat distribution is uneven in time, gradually decaying, and the warmer requires frequent re-heating for longer applications.

(c) The gel, and fluid heaters suffer from the same inconveniences in use. The heating action is uneven in time, decaying gradually, and the warmer needs re-heating about every hour for longer application. Moreover, the gel heating pads that contain gel in a plastic pouch may be inadvertently ruptured if placed under the body, resulting in a messy and potentially damaging spill of the gel. Warnings against bursting of the gel pouch under body weight are printed on the packaging of gel heating pads currently on the market.

(d) The warmers retaining body heat contain no external heat source and their effectiveness is therefore small. They are additional specialized pieces of clothing designed to retain more body heat than conventional clothing. They are tight and non breathable, and therefore retain perspiration.

Objects and Advantages

The objects and advantages of my body warmer are:

(a) to provide a body warmer that can be used for extended period of time without causing skin irritation and pain during removal;

(b) to provide a body warmer that enhances body heat production for greater effectiveness;

(c) to provide a body warmer with prolonged action at constant rate, thus eliminating the necessity of re-heating and handling warm heating pads;

(c) to provide a body warmer that does not reduce the mobility of the user;

(d) to provide a body warmer that can be used both in daytime and overnight. This feature allows the therapeutic use of body warmer during night rest, thus conditioning the body part needing therapy for daytime effort.

My body warmer consists in new use of rubefacient herbal material in the form of whole seed grains that is applied to the body in a container shell made of pliable and breathable material, equipped with fasteners to hold the shell in place.

Further objects and advantages of my invention will become apparent from a consideration of drawings and ensuing descriptions of the various embodiments of herbal warmers containing whole seed grains, and of new and unexpected results related to their use.

Drawing Figures

The drawings show typical embodiments of my body warmer, having various shapes and fastener configurations for use on various parts of the human body.

FIGS. 3 A to 3 D show a hand warmer mitt.

Figure 4A:
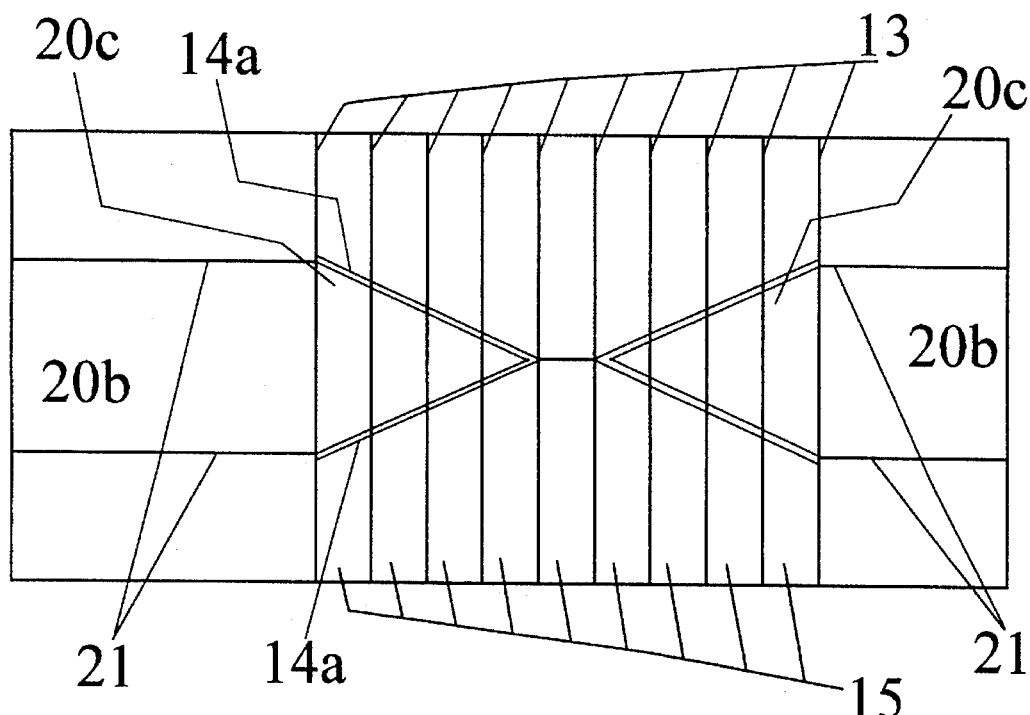
Figure 4B:
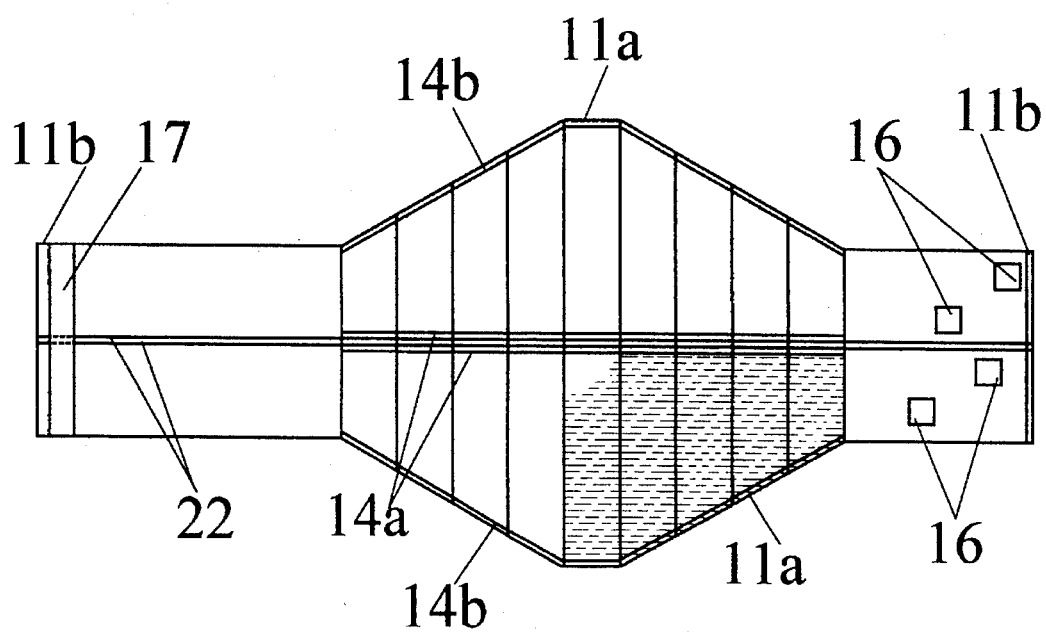

FIGS. 4 A and 4 B show an elbow, and knee warmer pad

FIGS. 5 A to 5 C show a foot warmer boot.

DESCRIPTION—FIGS. 1 to 5

The following descriptions include an explanation of the method of assembly of the various types of body warmers containing whole herb seed as this makes the description comprehensive and easy to follow.

Wrist, and ankle warmer

Figure 1:
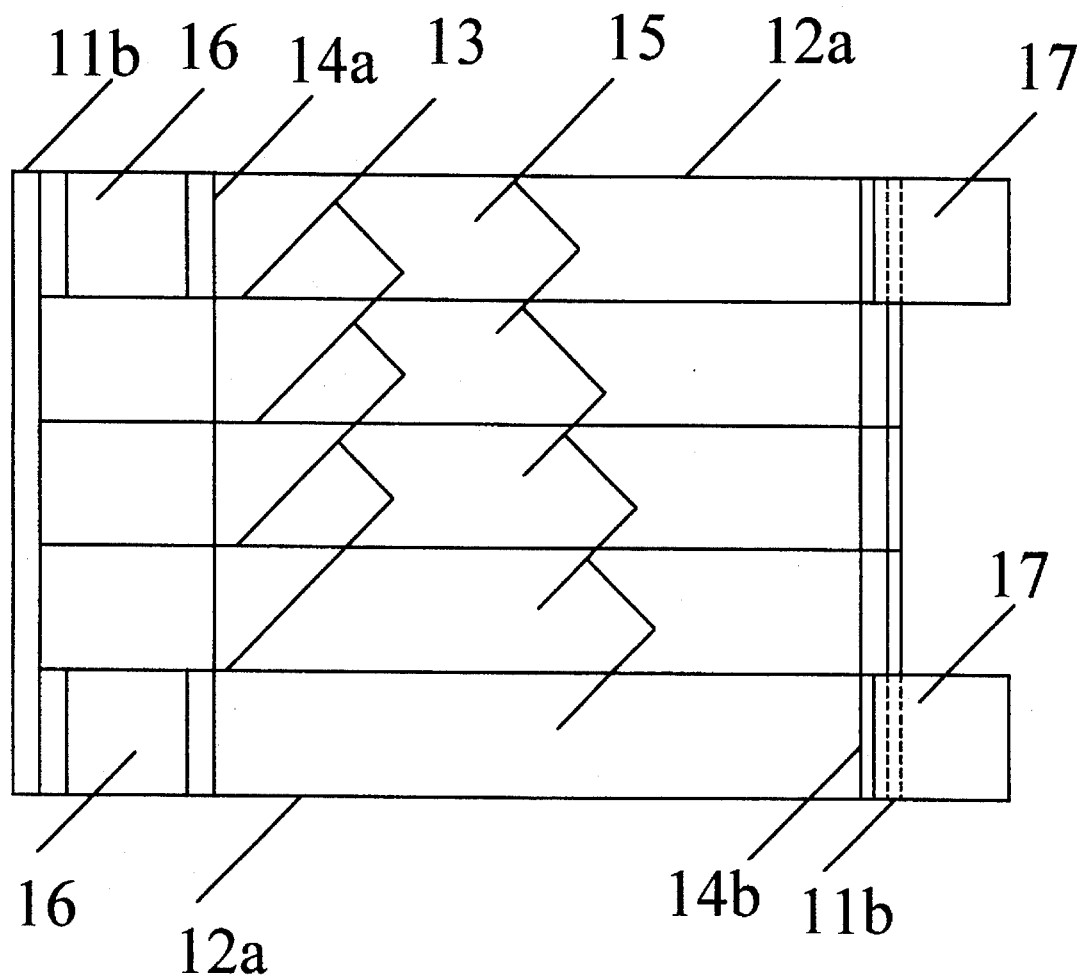
FIG. 1 shows a wrist, and ankle warmer pad.

A typical embodiment of a body warmer containing whole herb seed is illustrated in FIG. 1 showing a wrist, or ankle warmer. The warmer shell is made of two layers of fabric fastened together at two long sides by seams 12a made at the wrong side of fabric. The shell is then turned inside out, so that seams 12a are inside. Seams 13 are made next, to divide the shell into a number of tubular chambers 15. A seam 14a closing ends of chambers 15, is made, and chambers 15 are filled with herb seed. Seam 14b at the other end of chambers 15 is made next, to close chambers 15 filled with herb seed. Seams 11b reinforce the short ends of the shell. Hook-and-loop fasteners, each comprising a rectangular strip of loop unit 16, and a rectangular strip of hook unit 17 are attached to the reinforced short ends of shell.

Wrist and ankle warmers have the same structure, but differ in size. Dimensions of the fabric shell of a wrist warmer are typically 220 mm×110 mm. Dimensions of fabric shell of an ankle warmer are typically 300 mm×110 mm. Width of tubular chambers 15 (measured flat before filling herb seed) is 22 mm. Hook and loop fasteners are 22 mm wide. Loop unit strips 16 are 35 mm long, and hook unit strips 17 are 25 mm long.

Shoulder warmer

Figure 2:
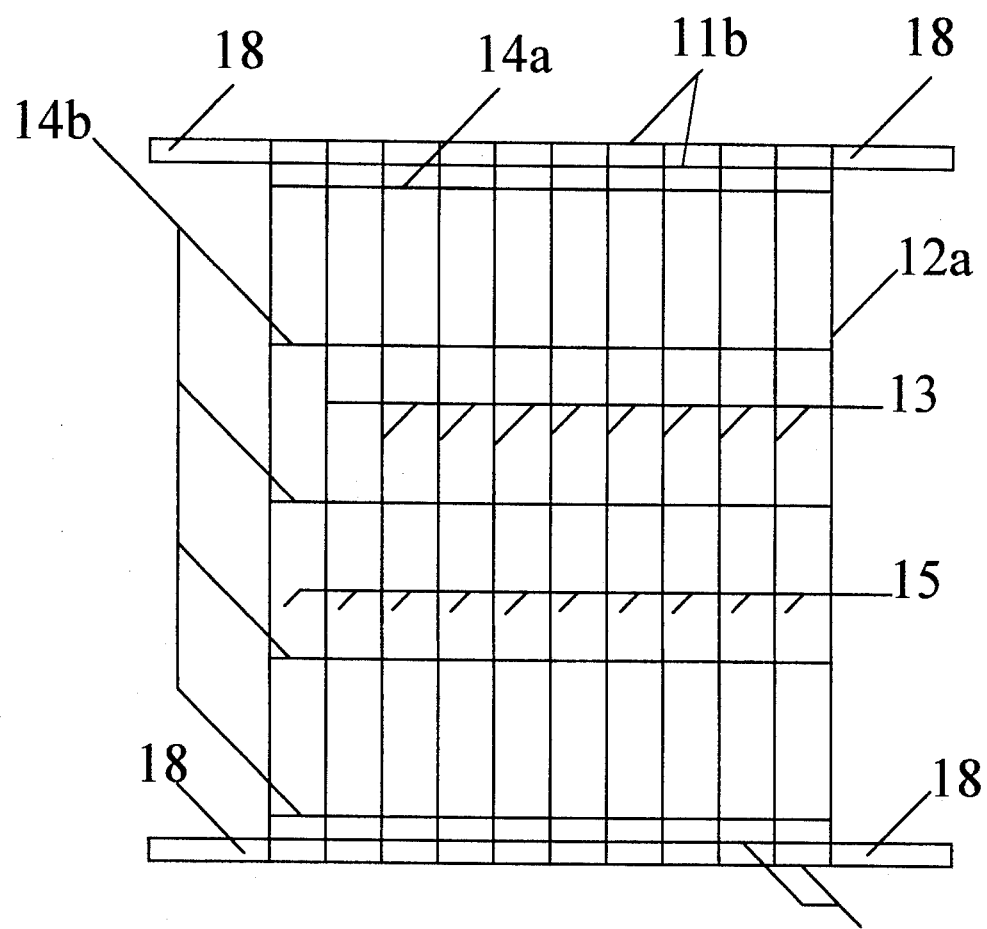
FIG. 2 shows a shoulder warmer pad.

A shoulder warmer pad is illustrated in FIG. 2. A shoulder warmer shell is made of two layers of fabric fastened along two long sides by seams 12a made on the wrong side of fabric. The shell is then turned inside out, so that seams 12a are inside. Seams 13 made next, divide the shell into a number of tubular chambers 15. Seam 14a ending chambers 15 along one of short ends of shell is made first, the first row of chambers 15 is filled with herb seed, and next seam 14b closing the first row of chambers 15 filled with herb seed is made. This operation is repeated for next three rows of chambers 15, each closed after filling with herb seed by a seam 14b. Seams 11b reinforce short ends of the shoulder warmer. Ribbon tie straps 18 attached to corners of the shell are used to fasten the shoulder warmer pad to the body.

Dimensions of the fabric shell of a shoulder warmer are typically 300 mm×250 mm. Tubular chambers 15 (measured flat before filling the herb seed) are 22 mm wide. Tie straps 18 are 250 mm long.

Hand warmer mitt

A hand warmer mitt is illustrated in FIGS. 3 A to 3 D. The fabric shell of a mitt consists of two rectangular layers of fabric with wrong sides facing inside, twice as long as the mitt (FIG. 3A). Seams 13 are made first along the shell to divide the shell into tubular chambers. The shell is then folded in half across the long dimension along line 19a, and long sides of the folded shell are fastened together by seams 12a. Seams 12a also attach ends of the hook-and-loop fastener straps 16 and 17 to the mitt shell (FIG. 3B). At this stage the mitt shell has two layers of chambers 15 separated by seams 13.

Figure 3A:
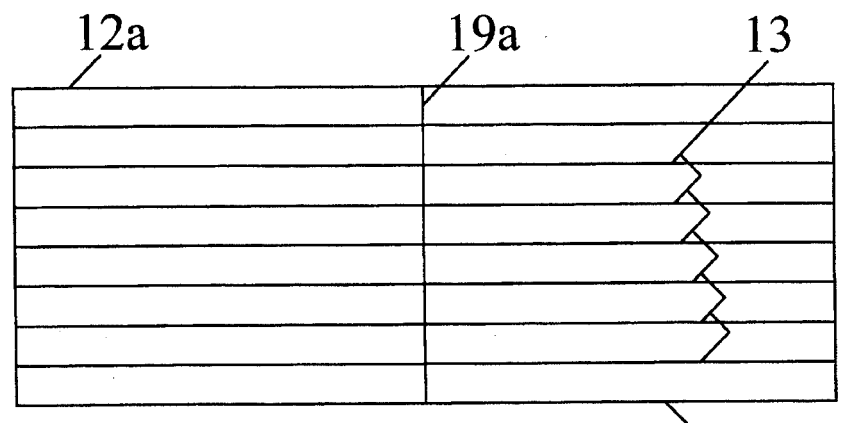
Figure 3B:
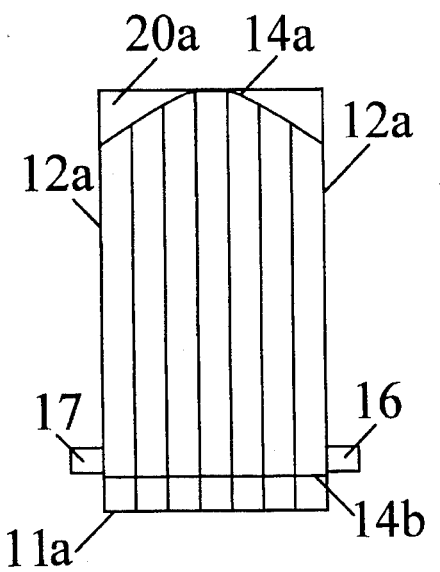
Figure 3C:
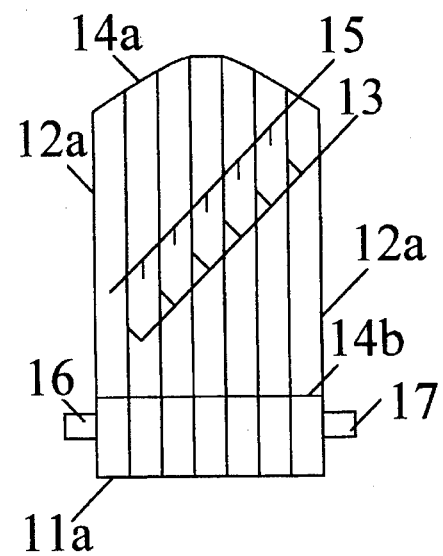

FIG. 3B is the view of the top hand side of a mitt. The arcuate end of a mitt is the finger tip end, and the straight end is the wrist end. The arcuate seam 14a closing the chambers 15 at the finger tip end of the shell is made next. The fabric shell is cut along seam 14a, the cut out area 20a is removed, and the mitt shell is then turned inside out, so that seams 12a and 14a are inside. Chambers 15 are filled with herb seed and seam 14b is made to close chambers 15 at wrist side. On the palm side of a mitt, shown in FIG. 3C, chambers 15 are filled with herb seed and seam 14b closing chambers 15 on the wrist side is made. On the palm side of a mitt chambers 15 containing herb seed are shorter than on the hand top side, to allow the shell to fold upon closure of hook and loop fastener straps 16 and 17. Seam 11a assembles the two layers of the shell fabric at the wrist end of a mitt.

Figure 3D:
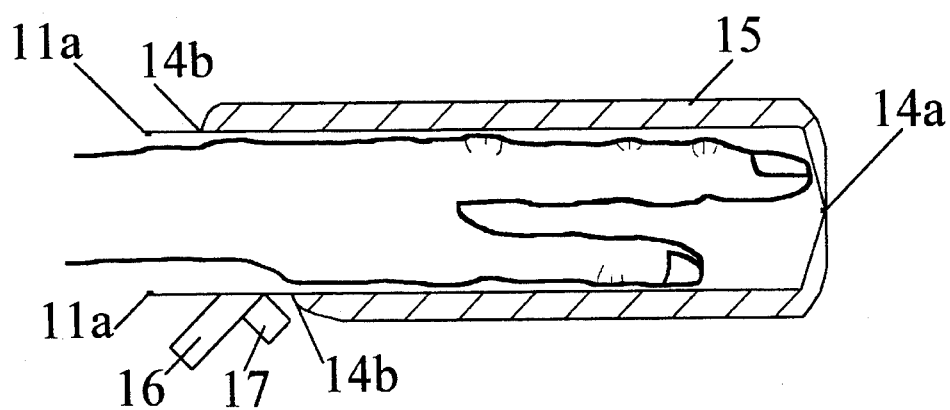

FIG. 3D shows the position of the hand inside a mitt. Hook-and-loop fasteners 16 and 17 are shown unfastened.

Typical dimensions of a mitt are 250×176 mm. Chambers 15 measured flat, before filling with herb seed are 22 mm wide. Hook-and-loop fastener straps 16 and 17 are 75 mm long and 12 mm wide.

Knee, and elbow warmer

A knee, and elbow warmer is shown in FIGS. 4 A and 4 B. Both knee and elbow warmers have similar structure but different dimensions. The shell of a knee, or elbow warmer (FIG. 4 A) comprise two rectangular layers of fabric. First, seams 13 are made across the long axis of the shell to divide the shell into tubular chambers 15. Seams 14a are made next. Rectangular areas 20b and triangular areas 20c of the shell are then cut out. The shell is folded along the long axis, and cut edges 21 (FIG. 4 A) are assembled by seam 22 (FIG. 4 B).

Seam 22 configures the warmer shell into a concave shape to accommodate a knee or an elbow. Tubular chambers 15 are then filled with herb seed, and seams 14b are made to close chambers 15. Seams 11a assemble the long edges of the shell. Loop unit tabs 16, and hook unit strip 17 of the hook-and-loop fastener are attached at the ends of the shell, and seams 11b are made along the short ends of the shell. The two rows of loop unit tabs 16 allow to adjust the tightness of the warmer around the elbow or the knee. Typical dimensions of an elbow warmer shell are: 430×280 mm. The width of the cut out is 65 mm. Tubular chambers 15 are 22 mm wide, measured flat between seams 13 before filling with herb seed.

The shell of a knee warmer is typically 510 mm long and 330 mm wide. The width of the cut out is 65 mm. Tubular chambers 15 are 22 mm wide, measured flat between seams 13 before filling with herb seed.

Foot warmer

Figure 5A:
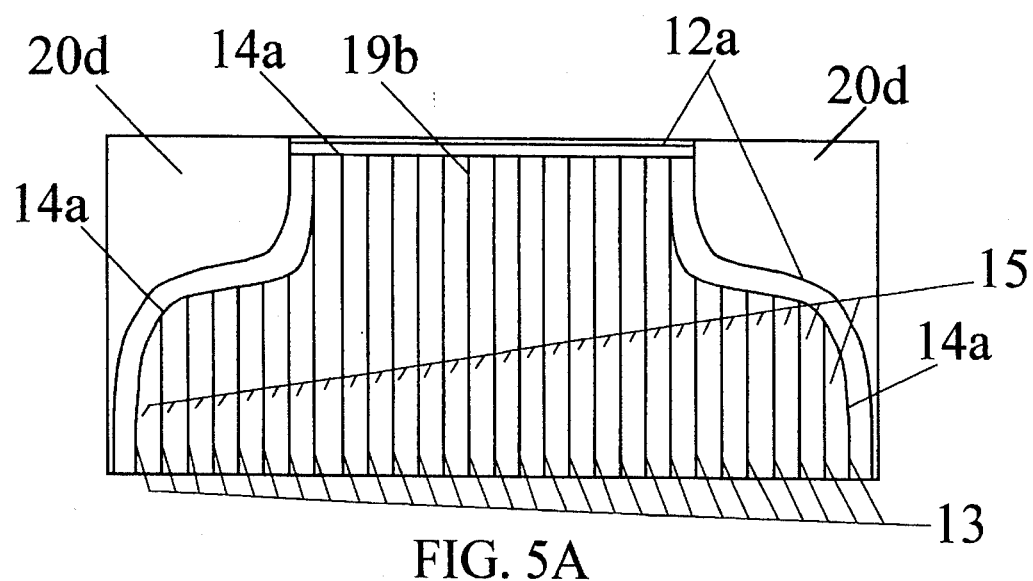
Figure 5B:
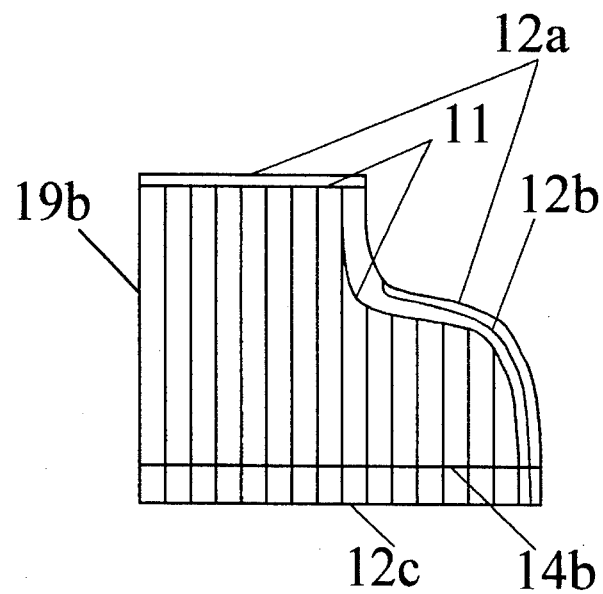
Figure 5C:
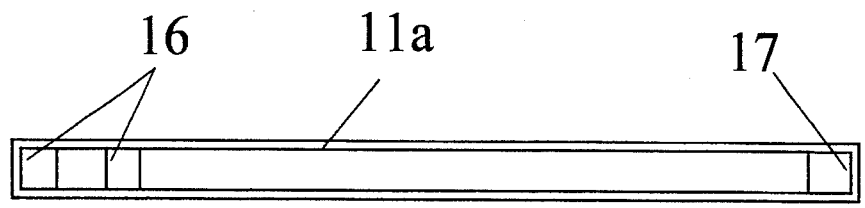

A foot warmer is shown in FIGS. 5A to 5C. The shell of a foot warmer consists of two rectangular layers of fabric (FIG. 5A) assembled by seam 12a on the wrong side and then turned inside out so that seam 12a is inside. Seam 14a is then made on the right side of the fabric shell and cut-out areas 20d are removed. Next, seams 13 are made to divide the shell into tubular chambers 15. The shell is then folded in two along line 19b, turned inside out and seam 12b is made (FIG. 5 B) to assemble the front part of foot warmer. The shell is turned inside out again, so that seam 12b is inside. Next, tubular chambers 15 are filled with herb seed, and seam 14b is made to close the tubular chambers at a distance of 1" from the edge of the shell. The shell is then turned inside out and seam 12c is made to close the sole of a boot-shaped foot warmer. The shell turned once more inside out, so that seam 12c is inside. The foot warmer is fastened around the ankle with a strap shown in FIG. 5C. The strap consists of two layers of fabric stitched along the edges and fitted with hook-and-loop fastener tabs. Two loop unit tabs 16 allow to adjust the tightness of the strap.

The dimension of the fabric shell of a foot warmer is typically 680 mm×360 mm. Tubular chambers 15 measured flat before filling the herb seed are 22 mm wide. The thstener strap is 450 mm long and 20 mm wide with hook and loop strips 50 mm long.

Operation—FIGS. 1, 2, 3, 4, 5

The manner of using body warmers containing whole herb seed is to wrap the warmer designed for the specific body part around that body part, for example the ankle warmer (FIG. 1 B) around the ankle, and fasten the warmer in place using the hook-and-loop fasteners (FIGS. 1, 3, and 4), tie straps (FIG. 2), or straps equipped with hook-and-loop fasteners (FIG. 5C). To use the hand warming mitt and the foot warmer one inserts the hand in the mitt (FIG. 3 C), and the foot into the foot warmer (FIG. 5). The body heat causes gradual release of vapors of rubefacient compounds from the herb seed. The vapors pass through the breathable shell of the body warmer and act on the body part surrounded by the warmer to enhance body heat production. These two processes result in a sustained heat level slightly above normal body temperature, that is perceived by the user of a body warmer as soothing and pleasant. The heating effect starts after about 10 minutes of wearing the body warmer, and lasts as long as the body warmer is in place. A balance between heat production rate and heat dissipation rate is established so that the heat never gets excessive, and the body warmers are safe for prolonged use, including overnight use.

The herb seed used to obtain enhanced body heat production is white mustard (botanical name *Brassica alba*) and black mustard (botanical name *Brassica nigra*). A combination of the two in proportion 35–45 percent of white mustard and 55–65 percent black mustard has been found empirically to produce best results.

Summary, Ramifications, and Scope

Accordingly, the reader will see that the body warmers using whole herb seed are safe and convenient for use, as they contain no electric or chemical components and do not require handling of hot warming pads or pouches. The fasteners keeping body warmers in place are easy to use.

The novel and unexpected results of the described body warmers are:

● The use of whole herb seed as the active rubefacient agent keeps the enhanced body heat production at a low level that can be safely sustained for several hours at a time. At the same time whole herb seed retains its rubefacient properties for a long period of time, empirically determined to last about a year.

● The herb seed, while not in direct contact with the body but separated from the body surface by the breathable shell of the body warmer, are sufficiently warmed by body heat to release vapors of the rubefacient compounds, thus initiating enhancement of body heat production. As the temperature gradient across the shell of the body warmer becomes steeper a balance of body heat production and heat dissipation keeps the warming effect at a steady level and prevent excessive heat build-up.

● The herb seed is robust, and although the individual seed grains move against each other during use, no abrasion was observed during an extensive test period of daily use.

As described above, the body warmers of this invention enhance body heat production for therapeutic action, and at the same time prevent excessive heat built-up. They can be used for extended periods of time, both during daytime and overnight. During daytime use they do not reduce the mobility of the user.

Although the description above contain many specificities, these should not be construed as limiting the scope of the invention but as merely providing illustrations of some of the presently preferred embodiments of this invention. For example body warmers for other body parts can have other shapes and fastener arrangements, etc.

Thus the scope of this invention should be determined by the appended claims and their legal equivalents, rather than by the examples given.

I claim:

1. A method of apyrogenic enhancement of body heat production by application of whole seed grains of rubefacient herbs selected from the group consisting of mustard herbs of the Brassica genus and herbs classified in the botanical family Cruciferae, contained in a breathable shell to the skin surface, whereby a balance of body heat enhancement by rubefacient herb seed and heat dissipation keeps the body warming effect at a steady level.

2. A warmer for part of human body to enhance body heat production by the apyrogenic method of claim 1, including said breathable shell, said shell comprising anelastic material, said material being pliable, said shell divided into a plurality of chambers containing said whole seed grains of rubefacient herbs, and means of attachment to hold the warmer in place on part of human body.

* * * * *